US008535237B2

(12) United States Patent
Nishtala

(10) Patent No.: US 8,535,237 B2
(45) Date of Patent: Sep. 17, 2013

(54) CONTINUOUS INTRA-ABDOMINAL PRESSURE MONITORING SYSTEM

(75) Inventor: Vasu Nishtala, Plano, TX (US)

(73) Assignee: C. R. Bard, Inc., Murray Hill, NJ (US)

( * ) Notice: Subject to any disclaimer, the term of this patent is extended or adjusted under 35 U.S.C. 154(b) by 451 days.

(21) Appl. No.: 12/739,492

(22) PCT Filed: Oct. 22, 2008

(86) PCT No.: PCT/US2008/080739
§ 371 (c)(1),
(2), (4) Date: Apr. 23, 2010

(87) PCT Pub. No.: WO2009/055435
PCT Pub. Date: Apr. 30, 2009

(65) Prior Publication Data
US 2010/0249663 A1  Sep. 30, 2010

Related U.S. Application Data

(60) Provisional application No. 60/981,978, filed on Oct. 23, 2007.

(51) Int. Cl.
*A61B 5/00* (2006.01)
(52) U.S. Cl.
USPC .......................................................... 600/561
(58) Field of Classification Search
USPC .................. 600/561; 604/544; 137/507, 455
See application file for complete search history.

(56) References Cited

U.S. PATENT DOCUMENTS

| 790,353 | A | 5/1905 | Estlingen |
| 1,666,332 | A | 4/1928 | Hirsch |
| 3,016,915 | A | 1/1962 | Moeller, Jr. |
| 3,157,201 | A | 11/1964 | Littmann |
| 3,411,534 | A | 11/1968 | Rose |
| 3,570,488 | A | 3/1971 | Diskin et al. |
| 3,805,830 | A | 4/1974 | Smith |
| 3,918,490 | A | 11/1975 | Goda |
| 3,985,134 | A | 10/1976 | Lissot et al. |
| 4,051,867 | A | 10/1977 | Forberg |
| 4,061,142 | A | 12/1977 | Tuttle |
| 4,217,911 | A | 8/1980 | Layton |
| 4,227,533 | A | 10/1980 | Godfrey |
| 4,300,571 | A | 11/1981 | Waldbillig |

(Continued)

FOREIGN PATENT DOCUMENTS

| WO | WO 9408152 A1 * | 4/1994 |
| WO | 96/02214 A1 | 2/1996 |

(Continued)

OTHER PUBLICATIONS

Balogh, Zsolt et al., "Continuous intra-abdominal pressure measurement technique," American Journal of Surgery, col. 188, No. 6, pp. 679-684, Dec. 2004.

(Continued)

*Primary Examiner* — Brian Szmal
(74) *Attorney, Agent, or Firm* — Rutan & Tucker, LLP

(57) ABSTRACT

Described herein are devices, systems, kits and methods for continuously measuring intra-abdominal pressure (IAP) from a patient catheterized with a urinary catheter system. Devices may include a lumen configured to connect to a pressure transducer, and a compensation chamber in fluid communication with the lumen and a urinary catheter.

19 Claims, 4 Drawing Sheets

(56) References Cited

U.S. PATENT DOCUMENTS

| | | | |
|---|---|---|---|
| 4,301,811 A | 11/1981 | Layton | |
| 4,425,113 A | 1/1984 | Bilstad | |
| 4,428,745 A | 1/1984 | Williams | |
| 4,545,389 A | 10/1985 | Schaberg et al. | |
| 4,673,389 A | 6/1987 | Archibald et al. | |
| 4,683,894 A | 8/1987 | Kodama et al. | |
| 4,714,463 A | 12/1987 | Archibald et al. | |
| 4,821,996 A | 4/1989 | Bellotti et al. | |
| 4,833,329 A | 5/1989 | Quint et al. | |
| 4,867,745 A | 9/1989 | Patel | |
| 4,966,161 A | 10/1990 | Wallace et al. | |
| 5,000,419 A | 3/1991 | Palmer et al. | |
| 5,082,025 A | 1/1992 | DeVries et al. | |
| 5,097,840 A | 3/1992 | Wallace et al. | |
| 5,097,868 A | 3/1992 | Betush | |
| 5,383,489 A * | 1/1995 | Golestan et al. | 137/504 |
| 5,385,563 A | 1/1995 | Gross | |
| 5,433,216 A | 7/1995 | Sugrue et al. | |
| 5,466,228 A | 11/1995 | Evans | |
| 5,520,636 A | 5/1996 | Korth et al. | |
| 5,823,972 A | 10/1998 | McRae | |
| 5,891,134 A | 4/1999 | Goble et al. | |
| 5,910,135 A | 6/1999 | Hadzic et al. | |
| 5,993,395 A | 11/1999 | Shulze | |
| 6,021,781 A | 2/2000 | Thompson et al. | |
| 6,117,086 A | 9/2000 | Shulze | |
| 6,159,160 A | 12/2000 | Hsei et al. | |
| 6,183,421 B1 | 2/2001 | Bobo | |
| 6,334,064 B1 | 12/2001 | Fiddian-Green | |
| 6,434,418 B1 | 8/2002 | Neal et al. | |
| 6,447,462 B1 | 9/2002 | Wallace et al. | |
| 6,503,208 B1 | 1/2003 | Skovlund | |
| 6,626,884 B1 | 9/2003 | Dillon et al. | |
| 6,632,190 B2 | 10/2003 | Simonini et al. | |
| 6,638,208 B1 | 10/2003 | Natarajan et al. | |
| 6,673,022 B1 | 1/2004 | Bobo et al. | |
| 6,673,051 B2 | 1/2004 | Flinchbaugh | |
| 6,719,709 B2 | 4/2004 | Whalen et al. | |
| 6,855,126 B2 | 2/2005 | Flinchbaugh | |
| 6,896,002 B2 | 5/2005 | Hart et al. | |
| 7,112,177 B2 | 9/2006 | Christensen et al. | |
| 7,381,190 B2 | 6/2008 | Sugrue et al. | |
| 7,892,181 B2 | 2/2011 | Christensen et al. | |
| 8,052,671 B2 | 11/2011 | Christensen et al. | |
| 2002/0082610 A1 | 6/2002 | Cioanta et al. | |
| 2002/0115906 A1 | 8/2002 | Miller | |
| 2003/0023134 A1 | 1/2003 | Tracey | |
| 2003/0023135 A1 | 1/2003 | Ulmsten et al. | |
| 2003/0023144 A1 | 1/2003 | Tracey et al. | |
| 2003/0027326 A1 | 2/2003 | Ulmsten et al. | |
| 2003/0028074 A1 | 2/2003 | Tracey et al. | |
| 2003/0028075 A1 | 2/2003 | Ulmsten et al. | |
| 2003/0028159 A1 | 2/2003 | Tracey et al. | |
| 2004/0078235 A1 | 4/2004 | Tallal | |
| 2004/0080519 A1 | 4/2004 | Haskin | |
| 2004/0176703 A1 | 9/2004 | Christensen et al. | |
| 2004/0230118 A1 | 11/2004 | Necola Shehada et al. | |
| 2006/0041496 A1 | 2/2006 | Amin | |
| 2006/0058702 A1 | 3/2006 | Christensen et al. | |
| 2006/0060248 A1 | 3/2006 | Fangmeier et al. | |
| 2006/0079804 A1 | 4/2006 | Sugrue et al. | |
| 2007/0038143 A1 * | 2/2007 | Christensen et al. | 600/561 |
| 2007/0255167 A1 | 11/2007 | Christensen et al. | |
| 2007/0282219 A1 | 12/2007 | Holte | |
| 2008/0027373 A1 | 1/2008 | Holte | |
| 2009/0221933 A1 * | 9/2009 | Nishtala et al. | 600/561 |

FOREIGN PATENT DOCUMENTS

| | | |
|---|---|---|
| WO | 03001974 A2 | 1/2003 |
| WO | 03001975 A2 | 1/2003 |
| WO | 03001977 A2 | 1/2003 |
| WO | 03001978 A2 | 1/2003 |
| WO | 03/071944 A1 | 9/2003 |
| WO | 2004071279 A2 | 8/2004 |
| WO | 2004/078235 A2 | 9/2004 |
| WO | 2004/080519 A1 | 9/2004 |
| WO | 2006041496 A1 | 4/2006 |
| WO | 2006060248 A2 | 6/2006 |

OTHER PUBLICATIONS

EP 06787204.4 filed Jan. 8, 2008 European Search Report dated Aug. 17, 2011.

JP 2008-521621 filed Jan. 11, 2008 Office Action dated Nov. 25, 2011.

Kron et al; The Measurement of Intra-abdominal Pressure as a Criterion for Abdominal Re-exploration, Ann Surg.; 199 (1): 28-30; Jan. 1984.

PCT/US06/27264 filed Jul. 15, 2006 International Search Report and Written Opinion dated Jul. 13, 2007.

U.S. Appl. No. 11/994,910, filed Dec. 22, 2008 Final Office Action dated May 1, 2012.

U.S. Appl. No. 11/994,910, filed Dec. 22, 2008 Non-Final Office Action dated Feb. 2, 2012.

* cited by examiner

CONTINUOUS INTRA-ABDOMINAL PRESSURE MONITORING SYSTEM

This application is a U.S. national stage application under 35 USC §371 of International Application No. PCT/US2008/080739, filed Oct. 22, 2008, which claims the benefit of priority to U.S. Provisional Application No. 60/981,978, filed Oct. 23, 2007, the contents of which are incorporated herein by reference in their entirety. In addition, this application contains subject matter related to International Application No PCT/US2006/027264, filed Jul. 13, 2006, the contents of which are incorporated herein by reference in their entirety.

BACKGROUND OF THE INVENTION

Intra-abdominal pressure (IAP) is an important parameter and prognostic indicator of a patient's underlying physiologic status. Correct IAP measurement is therefore crucial. One simple way of measuring IAP includes the measurement of bladder pressure. In particular, the measurement of bladder pressure via an indwelling urinary catheter system is a simple and effective way of indirectly measuring intra-abdominal pressure. Serial monitoring of bladder pressures is useful in detecting the onset of intra-abdominal hypertension (IAH) and the progression to the more severe condition, abdominal compartment syndrome (ACS). IAH and ACS occur when the abdominal contents expand in excess of the capacity of the abdominal cavity. Causes of IAH and ACS include intraperitoneal blood, interstitial edema from fluid resuscitation, peritonitis, ascites, and gaseous bowel distention. Both IAH and ACS have been primarily associated with trauma patients; however, patients with other pathological conditions are now being recognized as "at risk" for IAH and ACS.

Primary organ systems adversely affected by IAH and ACS include the cardiovascular, renal, pulmonary, gastrointestinal, and central nervous systems. Not only should patients be monitored for physiological changes, but intra-abdominal pressure also should be measured. Several techniques for measuring intra-abdominal pressure have been described in the literature, including a method described by Kron et al. (Kron, Hartman, and Nolan, "The measurement of intra-abdominal pressure as a criterion for abdominal re-exploration," Ann Surg, 199:28-30, 1984), which is incorporated by reference into this application as if fully set forth herein. These techniques include direct intraperitoneal measurement with a peritoneal dialysis catheter, intragastric measurement via a nasogastric tube, and measurement of pressure via the rectal route or through a urinary catheter system in the bladder. Although the intraperitoneal route is the most direct, the need for insertion of a special catheter into the peritoneum has inherent risks that make this method undesirable for widespread clinical use. Of the remaining options, measurement of bladder pressure via an indwelling urinary catheter system has become the method of choice because of its ease and reliability.

Measurements of bladder pressure should be undertaken as part of the examination of any patient at risk for IAH or ACS, and the measurement of intra-abdominal pressure should be correlated with other assessment findings associated with organ system compromise.

The bladder may act as a passive reservoir and accurately reflect intra-abdominal pressure when the intravesicular volume is approximately 100 mL or less. Bladder pressure can be measured easily by using a conventional pressure transducer system connected to the patient's urinary catheter drainage system. Currently, most bladder pressure measurements are done using devices constructed by medical professionals on an ad-hoc basis, who must assemble a pressure monitor using materials available in the hospital setting. Such home-made monitors require time to assemble, and may vary in quality, accuracy, and ease of use. As a result, the home-made monitors may be used less frequently than would be beneficial. Moreover, these monitors do not have a standardized level or performance or sterility. These devices may leak and may require interruption of the closed catheter system. Furthermore, certain commercially available systems require opening the Foley catheter system to use.

Applicant has recognized that it would be particularly advantageous to provide continuous measurements of IAP using commercially available urine catheters, such as Foley catheters. Applicant has also recognized that it would be advantageous to perform one or more IAP measurements from a urine catheter that is part of a catheterization system already in use by a patient, without having to open the system (e.g., by detaching the drainage tube, etc.), as opening the catheterization system may result in potentially exposing a patient or medical care provider to contamination or leakage of the system. Accordingly, devices, systems and methods for taking IAP measurements that may overcome one or more of these problems and/or others are described herein.

BRIEF SUMMARY OF THE INVENTION

Devices and systems for IAP monitoring, as well as kits and methods for using them, are described herein. These devices, systems, kits, and methods provide a way for a clinician or other medical practitioner to determine intra-abdominal pressure through pressure readings from a patient's bladder.

In particular, the devices for measuring and/or monitoring intra-abdominal pressure (IAP) from a patient may be devices that are to be used with a urinary catheter. Such a urinary catheter for use with devices according to the invention may include a retention balloon, for maintaining the position of the distal end of the catheter within the bladder, and a bypass lumen coupled to the retention balloon to provide fluid which may be used to inflate the balloon.

Accordingly, the devices for measuring and/or monitoring IAP described herein may be referred to as urinary catheter system bypass devices (or as "bypass devices"), because they allow measurement of IAP from the bypass lumen of a urinary catheter system or catheter system from a catheterized patient. One advantage of a system according to the invention is that such a system may allow measuring and/or monitoring of IAP preferably without having to disassemble or otherwise open the closed catheter system.

In certain embodiments of the invention, the bypass lumen is configured to be in fluid communication with a compensation chamber. The compensation chamber may be used to equilibrate pressure in the system such that changes in pressure in the system may be attributable substantially only to changes in pressure on the balloon walls. Such changes in pressure on the balloon walls typically are caused by changes to IAP.

The compensation chamber may be in fluid communication with a pressure transducer. The transducer may be used for measuring and/or monitoring intra-abdominal pressure ("IAP").

Thus, devices for measuring and/or monitoring intra-abdominal pressure from a patient catheterized with a urinary catheter system are described. In some variations, these devices are adapted to be used with catheters that have a sampling port and a drain tube. These devices may also include a retention balloon for location within the bladder.

Devices according to the invention may also include a fluid infuser (e.g., a pump such as a syringe, etc.) which may itself be connected to a fluid source for applying a bolus of fluid. In some variations, fluid pathways connecting the pressure transducer and a fluid pathway connecting the fluid infuser are part of the same fluid pathway. For example, the bypass lumen may be in fluid connection with a fluid pathway configured to connect to both a pressure transducer and a fluid infuser for infusing fluid though the bypass lumen.

Any appropriate fluid source may be used with the device (or as part of the device) for supplying fluid into the catheter. For example, the fluid source may be a saline source (e.g., saline bag), or the like. Furthermore, any appropriate fluid infuser may be used with the device (or as part of the device) for infusing fluid into the catheter. For example, a fluid infuser may be a fluid pump (e.g., a mechanical or electrical pump, etc.), including a syringe. In some variations, the fluid infuser is fluidly connected to a fluid source, so that fluid from the fluid source may be pumped through a lumen of the device and into the urinary catheter.

In certain embodiments of the invention, the fluid source and fluid infuser may be configured so that the device can be used continuously or, according to another embodiment, multiple times to measure IAP. In some variations, the fluid source and fluid infuser are connected with valves (e.g., one-way valves, flap valves, etc) that allow fluid to be drawn into the fluid infuser from the fluid source without drawing fluid through the bypass lumen when the fluid infuser operates in one direction (e.g., withdrawing the plunger of a syringe). Furthermore, flow between the fluid source and the fluid infuser can be prevented when the fluid infuser is delivering fluid through a lumen (e.g., pushing the plunger of a syringe).

In some variations, the fluid infuser includes a metered reservoir. For example, the fluid infuser delivers a metered amount of fluid for a single measurement. The metered amount or amounts may be pre-set (e.g., based on the volume available to the fluid infuser), or may be selected based on calibration marks on a portion of the fluid infuser. In some variations, the fluid infuser and the metered reservoir are part of a housing (e.g., the drain tube housing of the device). For example, the drain tube housing described above may include a fluid reservoir that can be loaded with fluid that can be controllably applied by the fluid infuser before and/or while making a measurement of IAP.

These and other embodiments, features and advantages will become more apparent to those skilled in the art when taken with reference to the following more detailed description of the invention in conjunction with the accompanying drawings that are first briefly described.

DESCRIPTION

The following description should be read with reference to the drawings. The drawings, which are not necessarily to scale, are not intended to limit the scope of the invention. The description illustrates by way of example, not by way of limitation, the principles of the invention. This description describes several embodiments, adaptations, variations, alternatives and uses of the invention.

Figure 1:
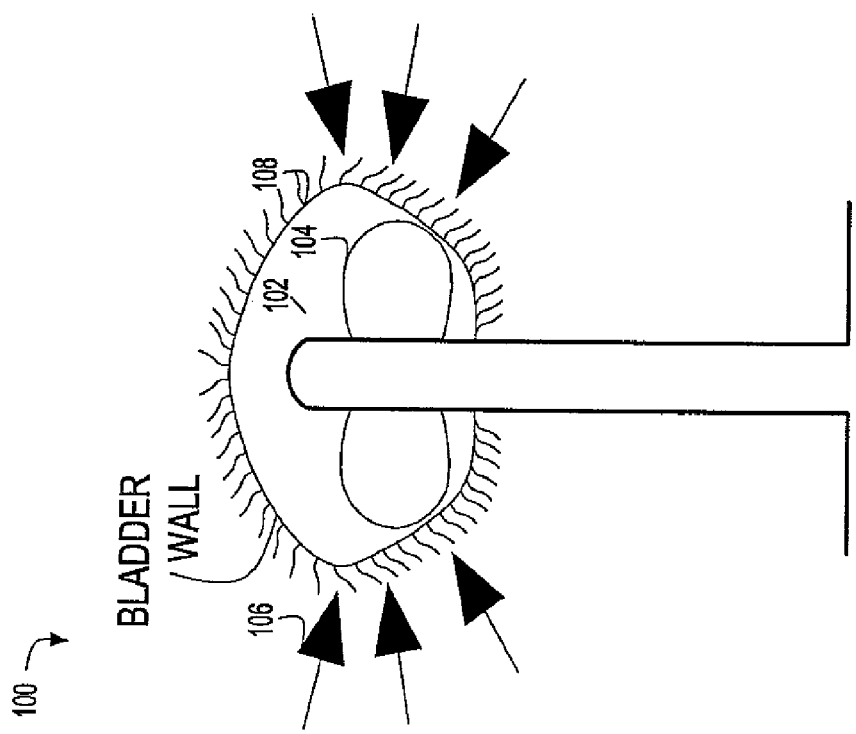
FIG. 1 shows a schematic view of a Foley catheter disposed according to the invention against the bladder walls.

In FIG. 1, a catheter device 100 is shown inserted into bladder 102. Retention balloon 104 maintains catheter device 100 in position within bladder 102. In one embodiment of a device according to the invention, balloon 104 may actually be configured to abut bladder walls 108. In such an embodiment, balloon 104 may be used to substantially continuously measure the IAP in real-time via pressure exerted on balloon 104 by bladder walls 108. Such a device preferably measures the IAP by monitoring changes to the fluid pressure (which may be a gas, liquid, or another suitable fluid medium) within balloon 104.

Figure 2:
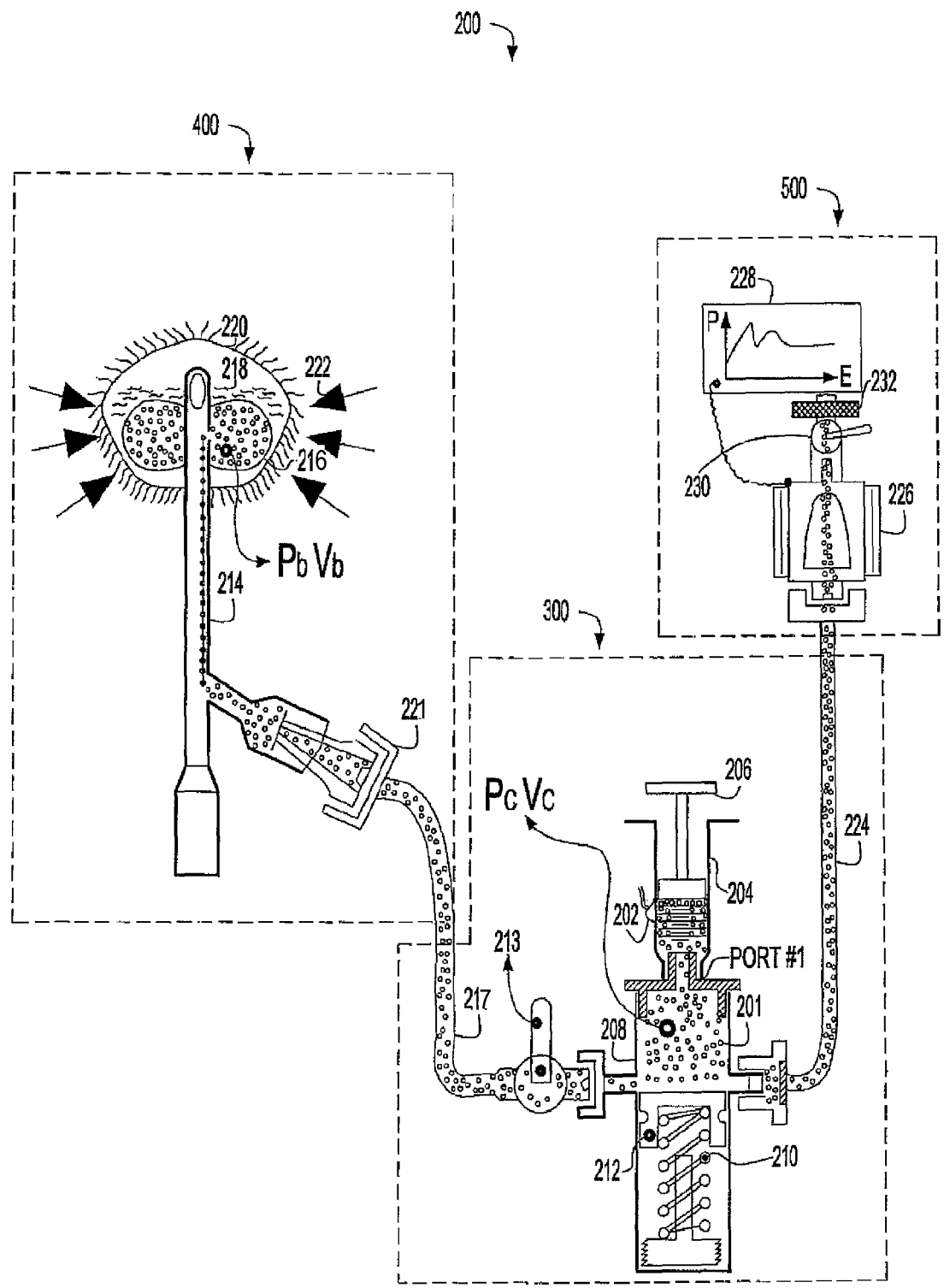
FIG. 2 shows a schematic diagram of a system for continuously monitoring IAP according to the invention.

FIG. 2 illustrates one variation of a continuous intra-abdominal pressure monitoring system 200 according to the invention. FIG. 2 shows a system 200 that includes exemplary sub-systems 300, 400, and 500. One, two, or all three of these subsystems may form at least a portion of a device according to the invention.

Subsystem 300 shows fluid 201. Subsystem 300 may include valve 202, syringe 204, syringe plunger 206, compensation chamber 208, compensation spring 210, and compensation chamber floor 212. Sub-system 300 may be coupled to sub-system 400 via lumen 217 which may be adapted to couple to a port in a Foley catheter on one end and may include a Foley stopcock on a second end.

Subsystem 400 may be a Foley catheter having a bypass lumen 214 therein, which is in fluid communication with retention balloon 216. Lumen 217 is also shown. Lumen 217 may couple subsystem 300 and subsystem 400 and promote fluid connection therebetween. Lumen 217 may be adapted to couple with a Luer interface, or any other suitable interface, at the port 221 of the bypass lumen 214. Lumen 217 may further include a stopcock 213 or other suitable device proximate the interface with subsystem 300, or at some other suitable location. Stopcock 213 may preferably selectably control the fluid communication between sub-system 300 and sub-system 400.

Subsystem 400 can also include retention balloon 216. Bladder walls 220 are also shown. Arrows 222 indicate the IAP on bladder walls 220. Changes in IAP 222 may cause balloon 216 to either expand, in response to a decrease of IAP, or contract, in response to an increase of IAP. In a device according to one embodiment, IAP is substantially continually, or periodically, sensed via change in fluid pressure within balloon 216.

Sub-system 500 can include a device for measuring and/or monitoring pressure within a self-contained fluid system. Specifically, sub-system 500 may include pressure transducer 226, monitor 228, Foley stopcock 230, and flow filter 232.

The device in FIG. 2 may operate as follows. Prior to priming the system for operation, the pressure in retention balloon 216 may be maintained at a constant value—e.g., at about 250 millimeters mercury (mm Hg)+/−5 mm Hg. Foley stopcock 213 is then set in a closed position. Transducer stopcock 230 is open.

In order to prime the system 200 so the system 200 can then monitor IAP, syringe 204 may be attached to the system. Syringe 204 may be filled with fluid. Syringe 204 may introduce fluid to compensation chamber 208 Port #1. When plunger 206 is depressed, fluid may be added to the system such that compensation chamber 208 and lumen 224 are filled with fluid. Flow filter 232 is attached to the system to allow air that was in the system prior to introduction of the fluid to escape from the system.

Next, transducer 226 is set to a baseline of zero using the compensation chamber 208, compensation chamber floor 212 and compensation spring 210, as will be explained. The zeroing out of the pressure in transducer 226 accommodates the existing, pre-determined, pressure in retention balloon 216, as will be explained.

In one embodiment of the invention, compensation chamber 208, compensation chamber floor 212 and compensation spring 210 are used to set the pressure and volume in chamber 208, PcVc, to substantially match the previously-determined pressure and volume in balloon 216, PbVb. Alternatively, just the pressure, Pc, is matched with pressure Pb in order to maintain the system at a pressure equilibrium such that any changes in system pressure may be substantially wholly attributable to changes in IAP, independent of any other pressure sources in the system.

Thereafter, stopcock 213 is opened to establish fluid communication between transducer 226, chamber 201, and retention balloon 216, and the entire system is equilibrated to a zero baseline value. Thus, in one embodiment of the invention, the new zeroed baseline for transducer 226 can be at about 250 mm Hg+/−5 mm Hg.

Accordingly, once a new baseline has been established for transducer 226, changes with respect to the baseline may indicate the changes in the IAP. Such changes may be on the order of between 10-20 mm Hg or even 5-30 mm Hg, depending on the internal characteristics of the patient. Spring 210 compression may be used to maintain proper pressure and volume in compensation chamber 212.

Following equilibration of the pressures Pb and Pc, Foley stopcock 213 may be opened to allow fluid communication between transducer 226, chamber 201, and retention balloon 216.

Once the system is primed, changes in IAP can be monitored as follows. First such changes in IAP change the pressure applied to the walls of balloons 216. Subsequently, if pressure increases on retention balloons 216, balloons 216 are compressed and the pressure is increased in the system. If pressure decreases on retention balloons 216, balloons 216 expand and decrease pressure in the system.

The pressure in the system may be continuously monitored by transducer 226. Transducer 226 is in fluid connection via catheter 214, lumen 217, chamber 201 and lumen 224 with balloon 216.

Transducer 226 is preferably electrically connected to monitor 228. Monitor 228 includes a display which may display the bladder pressure as it changes over time. Devices according to the invention can monitor changes to the abdominal pressure of the patient continuously without requiring removal of the catheter 214. Accordingly, such devices can prevent leakage and reduce the risk of infection.

Figure 3:
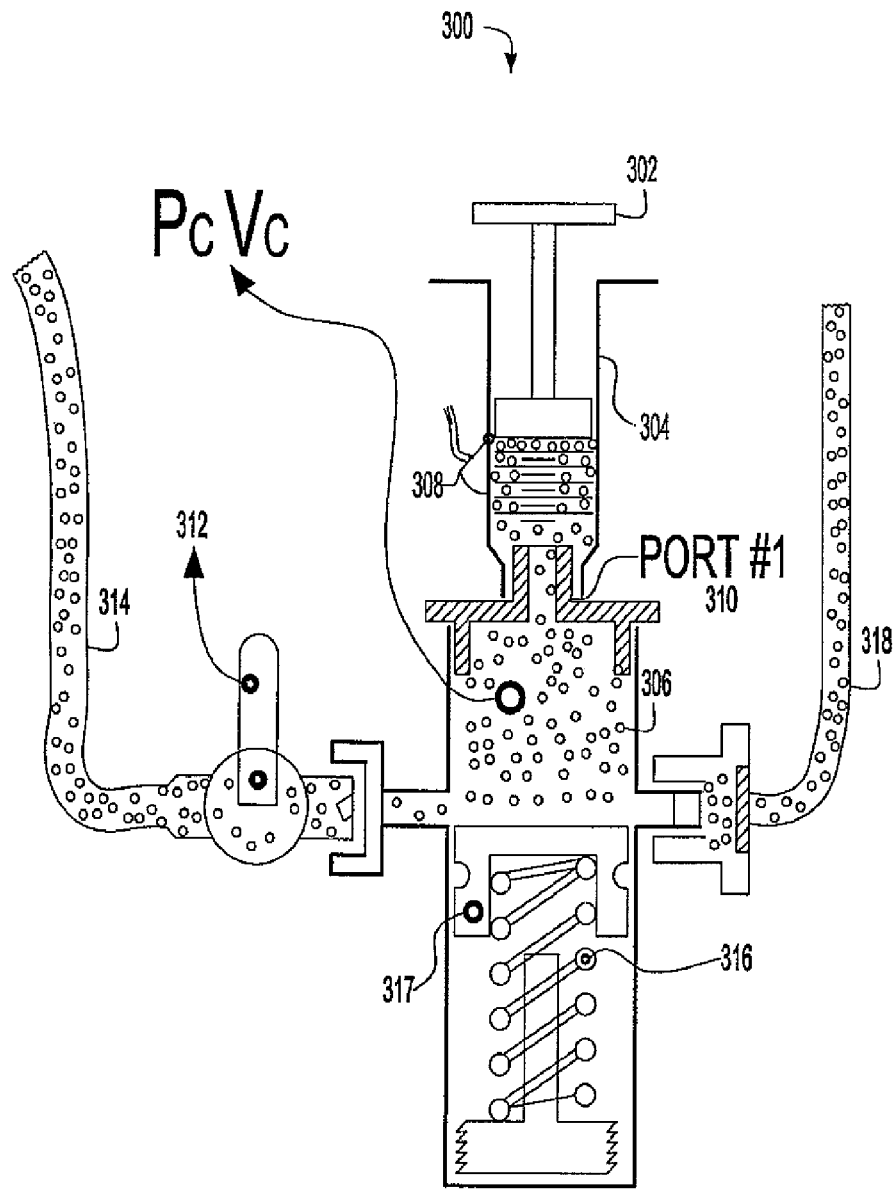
FIG. 3 shows an enlarged schematic diagram of one of the sub-systems of the system shown in FIG. 2.

FIG. 3 shows an enlarged schematic diagram of sub-system 300 shown in FIG. 2. As described above, the IAP monitoring can occur on a continuous basis. In order to prime the system, plunger 302 of syringe 304 may be pushed downward to compress the fluid in the system and cause fluid to enter compensation chamber 306. Fluid may also be introduced through valve 308 as needed. Valve 308 can allow the insertion of additional fluid without releasing the pressure in the system.

Downward movement of plunger 302 forces fluid through Port #1 310. Once sufficient fluid is introduced into the system, the system may be equilibrated using compensation spring 316, as described above. Specifically, adjusting compensation spring 316 resizes compensation chamber 306, and, consequently adjusts the pressure in the system, via movement of compensation chamber floor 317. Valve 308 is also shown. Valve 308 preferably allows for introduction of additional fluid into the system, following the use of the syringe. Lumen 314 preferably provides for fluid communication between subsystems 300 and 400, and lumen 318 preferably provides for fluid communication between subsystems 300 and 500.

Figure 4:
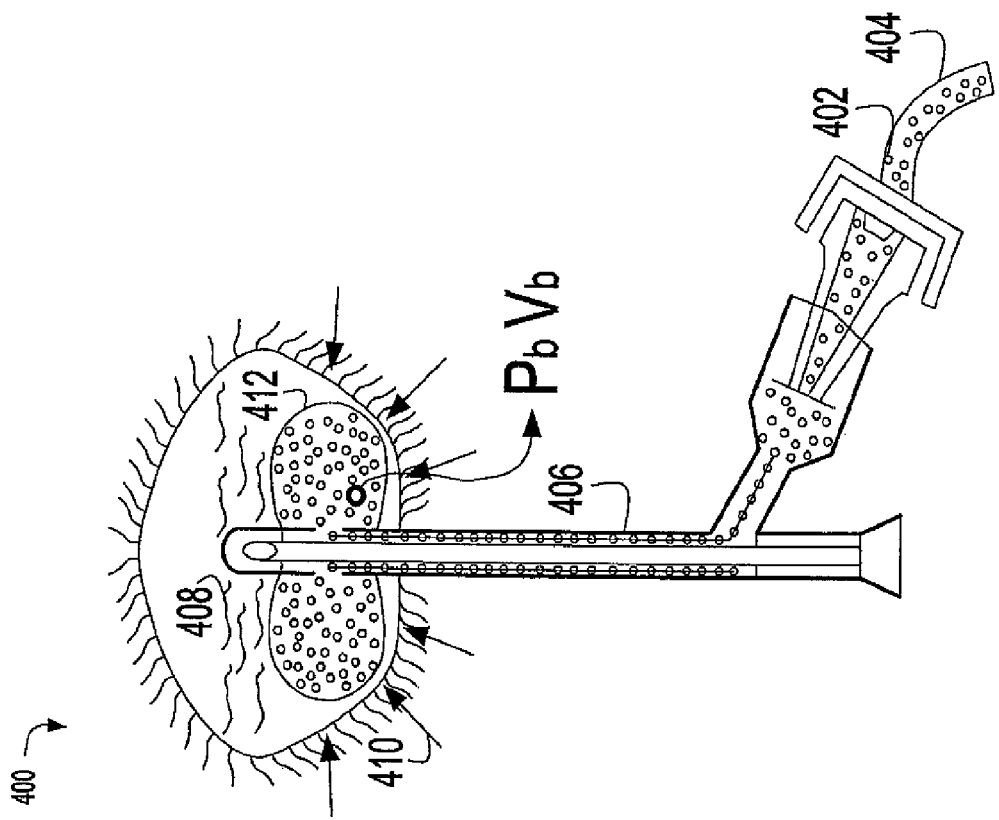
FIG. 4 shows an enlarged schematic diagram of another of the sub-systems of the system shown in FIG. 2.

FIG. 4 shows an enlarged schematic diagram of another one of the sub-systems shown in FIG. 2. In FIG. 4, the walls of retention balloon 412 abut the walls of bladder 408. In such an embodiment, changes in IAP preferably immediately invoke changes to the fluid pressure of the device system via the bladder walls. Also shown in FIG. 4 are the end of lumen 404, port 402, which couples lumen 404 to bypass lumen 406, and IAP pressure indicating arrows 410. Bypass lumen 406 is illustrated as a concentric lumen that surrounds a primary lumen. Such a primary lumen may be used to remove urine from the bladder. Nevertheless, bypass lumen 406 may be formed in any suitable shape or configuration that allows fluid to be transmitted from outside the body to the retention balloon independent of the primary lumen.

Figure 5:
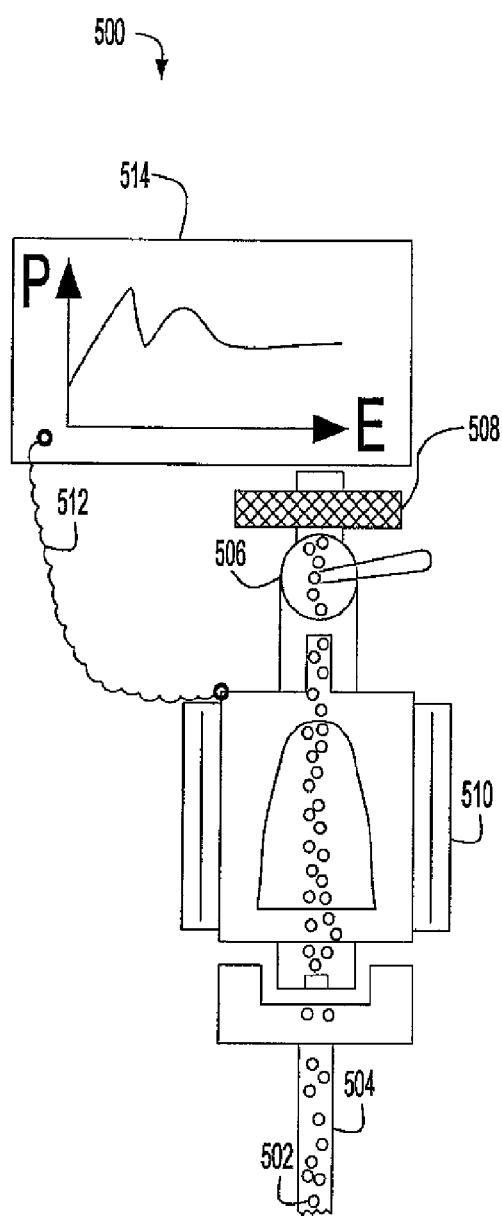
FIG. 5 shows an enlarged schematic diagram of yet another of the sub-systems of the system shown in FIG. 2.

FIG. 5 shows an enlarged schematic diagram of yet another one of the sub-systems shown in FIG. 2. In FIG. 5, the system may be primed by using flow filter 508 to allow air to escape from the system, as necessary. Once air has been released from the system, stopcock 506 may preferably be closed. Once the system is fully primed, any pressure changes may be detected by transducer 510 and transmitted from transducer 510 to monitor 514 either via wire 512, or, in one embodiment, wirelessly. The results may be stored by monitor 514 and/or displayed thereon. Monitor 514 may preferably display a trace of the pressure measurements (and/or changes to pressure measurements) P with respect to elapsed time E.

An additional point that shows the efficacy of the invention is the substantially similar characteristics exhibited by different retention balloons. Tables 1 and 2 show tests performed on 10 different balloons using air and water as materials for expanding the balloons. It can be seen from the bold-bordered areas that the balloons exhibited repeatable and consistent expandability characteristics. This property is evidenced from the low standard deviation shown across the bold-bordered areas in Tables 1 and 2.

TABLE 1

Air Test: 20 PSI, 20 CC, Fast method, Fast Sampling (13/S)

| Cath. Id. | Balloon Pressure | | Balloon Shape (MM) | | | | | Infl. Time | Area PSI × S |
|---|---|---|---|---|---|---|---|---|---|
| | Max PSI | Last PSI | Dia. | A | B | B/A | A:B | | |
| 1A | 17.96 | 8.34 | 28.43 | 13.39 | 15.04 | 1.12 | 47:53 | 0.62 | 4.92 |
| 2A | 19.15 | 9.24 | 27.85 | 13.28 | 14.57 | 1.10 | 48:52 | 0.62 | 5.47 |
| 3A | 18.86 | 8.87 | 28.02 | 12.40 | 15.62 | 1.26 | 44:56 | 0.62 | 3.96 |

TABLE 1-continued

Air Test: 20 PSI, 20 CC, Fast method, Fast Sampling (13/S)

| | | | | | | | | | |
|---|---|---|---|---|---|---|---|---|---|
| 4A | 19.68 | 9.18 | 27.58 | 13.72 | 13.86 | 1.01 | 50:50 | 0.69 | 4.85 |
| 5A | 18.18 | 8.45 | 28.52 | 13.00 | 15.52 | 1.19 | 46:54 | 0.62 | 4.12 |
| 6A | 19.69 | 9.26 | 27.69 | 13.55 | 14.14 | 1.04 | 49:51 | 0.62 | 5.95 |
| 7A | 19.01 | 8.86 | 28.41 | 14.08 | 14.33 | 1.02 | 50:50 | 0.62 | 5.66 |
| 8A | 18.98 | 8.79 | 28.12 | 13.36 | 14.76 | 1.10 | 48:52 | 0.69 | 5.17 |
| 9A | 19.18 | 8.84 | 27.59 | 12.83 | 14.76 | 1.15 | 47:53 | 0.69 | 6.08 |
| 10A | 19.57 | 9.11 | 27.81 | 12.13 | 15.68 | 1.29 | 44:56 | 0.77 | 6.53 |
| Average | 19.03 | 8.89 | 28.00 | 13.17 | 14.83 | 1.13 | 47:53 | 0.66 | 5.27 |
| St. Dev. | 0.5858833 | 0.316516 | 0.36 | 0.60 | 0.63 | 0.10 | | 0.052 | 0.833 |

| | Balloon Thickness | | | | | | |
|---|---|---|---|---|---|---|---|
| Cath. Id. | Mid. | Left | Right | Top | Bottom | Ave. | Std. Dev. |
| 1A | 0.0270 | 0.0270 | 0.0275 | 0.0270 | 0.0265 | 0.0270 | 0.0003536 |
| 2A | 0.0285 | 0.0300 | 0.0285 | 0.0290 | 0.0285 | 0.0289 | 0.0006519 |
| 3A | 0.0300 | 0.0290 | 0.0270 | 0.0290 | 0.0295 | 0.0289 | 0.0011462 |
| 4A | 0.0280 | 0.0285 | 0.0285 | 0.0285 | 0.0280 | 0.0283 | 0.0002739 |
| 5A | 0.0280 | 0.0275 | 0.0280 | 0.0275 | 0.0275 | 0.0277 | 0.0002739 |
| 6A | 0.0285 | 0.0290 | 0.0275 | 0.0295 | 0.0280 | 0.0285 | 0.0007906 |
| 7A | 0.0285 | 0.0290 | 0.0290 | 0.0285 | 0.0275 | 0.0285 | 0.0006124 |
| 8A | 0.0300 | 0.0300 | 0.0290 | 0.0295 | 0.0285 | 0.0294 | 0.0006519 |
| 9A | 0.0275 | 0.0290 | 0.0275 | 0.0275 | 0.0275 | 0.0278 | 0.0006708 |
| 10A | 0.0285 | 0.0295 | 0.0270 | 0.0280 | 0.0280 | 0.0282 | 0.0009083 |
| | | | | | | 0.0283 | 0.0006925 |
| Average | 0.0285 | 0.0289 | 0.0280 | 0.0284 | 0.0280 | | |
| St. Dev. | 0.001 | 0.001 | 0.00076 | 0.00088 | 0.0008 | | |

TABLE 2

Water Test: 30 PSI, 10 CC, Fast method, Fast Sampling (13/S)

| | Balloon Pressure | | Balloon Shape (MM) | | | | | Infl. | Area |
|---|---|---|---|---|---|---|---|---|---|
| Cath. ID | Max PSI | Last PSI | Dia. | A | B | B/A | A:B | Time | PSI × S |
| 1W | 36.01 | 8.76 | 28.43 | 11.63 | 6.80 | 1.44 | 41:59 | 3.69 | 101.23 |
| 2W | 36.46 | 9.11 | 27.33 | 13.24 | 4.09 | 1.06 | 48:52 | 3.16 | 85.97 |
| 3W | 36.28 | 9.17 | 27.31 | 9.99 | 7.32 | 1.73 | 37:63 | 3.62 | 95.10 |
| 4W | 35.85 | 8.75 | 27.29 | 11.31 | 5.98 | 1.41 | 41:59 | 3.69 | 97.15 |
| 5W | 35.53 | 9.10 | 27.54 | 11.94 | 5.60 | 1.31 | 43:57 | 3.46 | 83.17 |
| 6W | 36.06 | 8.87 | 27.71 | 12.74 | 4.97 | 1.18 | 46:54 | 3.38 | 87.21 |
| 7W | 36.20 | 9.34 | 27.04 | 13.11 | 3.93 | 1.06 | 48:52 | 3.54 | 90.97 |
| 8W | 35.79 | 9.21 | 27.72 | 12.05 | 5.67 | 1.30 | 43:57 | 4.23 | 106.13 |
| 9W | 35.80 | 9.00 | 27.17 | 12.56 | 4.61 | 1.16 | 46:54 | 3.23 | 80.84 |
| 10W | 35.05 | 8.61 | 27.08 | 10.39 | 6.69 | 1.61 | 38:62 | 3.31 | 82.84 |
| Average | 35.90 | 8.99 | 27.46 | 11.90 | 5.57 | 1.33 | 43:57 | 3.53 | 91.06 |
| St. Dev. | 0.40409157 | 0.235504 | 0.42 | 1.09 | 1.16 | 0.22 | | 0.308 | 8.5567 |

| | Balloon Thickness | | | | | | |
|---|---|---|---|---|---|---|---|
| Cath. ID | Mid. | Left | Right | Top | Bottom | Ave. | Std. Dev. |
| 1W | 0.0260 | 0.0295 | 00270 | 0.0265 | 3.69 | 0.0271 | 0.0013874 |
| 2W | 0.0275 | 0.0275 | 0.0275 | 0.02751 | 0.0275 | 0.0275 | 0 |
| 3W | 0.0270 | 0.0290 | 0.0290 | 0.0275 | 0.0280 | 0.0281 | 0.0008944 |
| 4W | 0.0270 | 0.0275 | 0.0270 | 0.0275 | 0.0275 | 0.0273 | 0.0002739 |
| 5W | 0.0285 | 00300 | 0.0285 | 0.0275 | 0.0290 | 0.0287 | 0.0009083 |
| 6W | 0.0280 | 0.0285 | 0.0280 | 0.0285 | 0.0275 | 0.0281 | 0.0004183 |
| 7W | 90.97 | 0.0285 | 0.0295 | 0.0295 | 0.02951 | 0.0291 | 0.0005477 |
| 8W | 0.0285 | 0.0295 | 0.0275 | 0.0290 | 0.0285 | 0.0286 | 0.0007416 |
| 9W | 0.0280 | 0.0285 | 0.0280 | 0.0280 | 0.0270 | 0.0279 | 0.0005477 |
| 10W | 0.0290 | 0.0270 | 0.0285 | 0.0290 | 0.0285 | 0.0284 | 0.0008210 |
| | | | | | | 0.0281 | 0.0003868 |
| Average | 0.0278 | 0.0287 | 0.0281 | 0.0281 | 0.0279 | | |
| St. Dev. | 0.0009 | 0.001 | 0.00083 | 0.00093 | 0.00078 | | |

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

Although the devices described herein are for use in measuring and/or monitoring IAP, it should be understood that they may be used for other applications instead of, or in addition to, measuring and/or monitoring IAP. These devices may be used anytime it is desirable to increase the pressure within the bladder, or within a catheter system. For example, the devices may be useful for rinsing a catheter system to remove blockage. Other variations are also within the scope of the methods, devices and systems described herein.

Finally, all publications and patent applications cited in this specification are herein incorporated by reference in their entirety as if each individual publication or patent application were specifically and individually put forth herein.

What is claimed is:

1. A system for monitoring intra-abdominal pressure, comprising:
    a pressure transducer;
    a lumen configured to connect to the pressure transducer;
    a compensation chamber connected to the lumen and configured to be removably attached to a port of a urinary catheter system to form a fluid connection between the urinary catheter system and the lumen, an interior volume of the compensation chamber configured to change to adjust fluid pressure within the device.

2. The system of claim 1, wherein the lumen is connected indirectly to the pressure transducer.

3. The system of claim 2 further comprising a stopcock that is configured selectably control a fluid connection between the compensation chamber and the pressure transducer.

4. The system of claim 1, wherein the compensation chamber comprises a spring.

5. The system of claim 1, wherein the compensation chamber comprises a port configured to securely receive a syringe.

6. The system of claim 1 further comprising a stopcock that is configured to selectably control the fluid connection between the compensation chamber and the urinary catheter system.

7. The system of claim 1 further comprising a second lumen that couples the urinary catheter system and the compensation chamber, and allows for a fluid connection therebetween.

8. The system of claim 1 further comprising the urinary catheter system, the urinary catheter system comprising a bypass lumen and a retention balloon, the retention balloon adapted to be expanded to at least partially abut at least a portion of the bladder wall of a patient, the retention balloon being in fluid communication with the compensation chamber.

9. The device of claim 1, wherein the compensation chamber comprises a compensation spring that is configured to bias a compensation chamber floor to change the interior volume of the compensation chamber.

10. The device of claim 1, wherein the device is configured to connect to the urinary catheter system during use thereof without having to disassemble or otherwise open a portion of the urinary catheter system to the atmosphere.

11. An Infra-Abdominal Pressure monitoring device comprising:
    a urinary catheter system comprising a bypass lumen and a retention balloon, the retention balloon adapted to be expanded to at least partially abut at least a portion of a bladder wall of a patient;
    a compensation chamber coupled by a fluid connection with the retention balloon via the bypass lumen, the compensation chamber being configured for adjusting fluid pressure within the device via movement of a compensation chamber floor; and
    a pressure monitor for monitoring pressure within the bladder, the pressure monitor being in fluid communication with the compensation chamber.

12. The device of claim 11, wherein the bypass lumen is connected indirectly to a pressure transducer.

13. The device of claim 12 further comprising a stopcock that is configured to selectably control a fluid connection between the compensation chamber and the pressure transducer.

14. The device of claim 11, wherein the compensation chamber comprises a compensation spring that is configured to bias the compensation chamber floor to adjust the volume of the compensation chamber.

15. The device of claim 11, wherein the compensation chamber comprises a port configured to securely receive a syringe.

16. The device of claim 11 further comprising a stopcock that is configured to selectably control the fluid connection between the compensation chamber and the urinary catheter system.

17. The device of claim 11, further comprising a syringe for injecting fluid into the compensation chamber, and a valve for adding or removing fluid from the compensation chamber.

18. The device of claim 17, wherein the valve is located on the syringe.

19. The device of claim 17, wherein the valve is located on the compensation chamber.

* * * * *